(12) United States Patent
Sekimizu et al.

(10) Patent No.: US 11,213,058 B2
(45) Date of Patent: Jan. 4, 2022

(54) POLYSACCHARIDE HAVING INNATE IMMUNITY STIMULATING ACTIVITY

(71) Applicant: IMAGINE GLOBAL CARE CORPORATION, Tokyo (JP)

(72) Inventors: Kazuhisa Sekimizu, Tokyo (JP); Makoto Urai, Tokyo (JP)

(73) Assignee: Imagine Global Care Corporation, Tokyo (JP)

( * ) Notice: Subject to any disclaimer, the term of this patent is extended or adjusted under 35 U.S.C. 154(b) by 223 days.

(21) Appl. No.: 16/309,098

(22) PCT Filed: Aug. 4, 2017

(86) PCT No.: PCT/JP2017/029237
§ 371 (c)(1),
(2) Date: Dec. 12, 2019

(87) PCT Pub. No.: WO2018/030542
PCT Pub. Date: Feb. 15, 2018

(65) Prior Publication Data
US 2020/0138080 A1 May 7, 2020

(30) Foreign Application Priority Data
Aug. 9, 2016 (JP) .............................. JP2016-156274

(51) Int. Cl.
*A23L 33/125* (2016.01)
*A23L 19/00* (2016.01)

(52) U.S. Cl.
CPC ............. *A23L 33/125* (2016.08); *A23L 19/00* (2016.08)

(58) Field of Classification Search
CPC .............................. A23L 19/00; A23L 33/125
See application file for complete search history.

(56) References Cited

U.S. PATENT DOCUMENTS 8,313,779 B2  11/2012  Sekimizu et al.
2004/0024199 A1  2/2004  Giori et al.
(Continued)

FOREIGN PATENT DOCUMENTS

CA  2016948 A1  11/1990
CN  1447695 A  10/2003
(Continued)

OTHER PUBLICATIONS

Ochoa-Villarreal M et al, "Plant Cell Wall Polymers: Function, Structure and Biological Activity of Their Derivatives." in: "Polymerization", licensee InTech (2012), p. 68, section 3.3.1 (Year: 2012).*
(Continued)

*Primary Examiner* — Nikki H. Dees
*Assistant Examiner* — Jeffrey D Benson
(74) *Attorney, Agent, or Firm* — Knobbe, Martens, Olson & Bear, LLP

(57) ABSTRACT

A substance having innate immune stimulating activity is a polysaccharide, which contains 25 to 50 parts by mole of galacturonic acid, 15 to 50 parts by mole of galactose, 0 to 7 parts by mole of glucose, 0 to 30 parts by mole of arabinose, 0 to 6 parts by mole of xylose, and 3 to 15 parts by mole of rhamnose as constituent sugars. The polysaccharide has a polygalacturonic acid chain having α-1,4-linked galacturonic acid as a main chain. An innate immune stimulant can include the polysaccharide as an active component, which can be included in a food or drink.

5 Claims, 7 Drawing Sheets

(56) References Cited

U.S. PATENT DOCUMENTS

| | | | |
|---|---|---|---|
| 2007/0059317 | A1 | 3/2007 | ElSohly et al. |
| 2009/0047405 | A1 | 2/2009 | Zhang |
| 2010/0111870 | A1 | 5/2010 | Sekimizu et al. |
| 2016/0151485 | A1 | 6/2016 | Albers et al. |

FOREIGN PATENT DOCUMENTS

| | | | | |
|---|---|---|---|---|
| EA | 006318 | B1 | 10/2005 | |
| EP | 2133693 | B1 | 6/2016 | |
| EP | 3498737 | | 6/2019 | |
| JP | 2-45501 | A | 2/1990 | |
| JP | 3-79602 | A | 4/1991 | |
| JP | 4-76003 | A | 3/1992 | |
| JP | 5714329 | B2 | 5/2015 | |
| KR | 10-2003-0091760 | | 12/2003 | |
| KR | 10-2005-0112071 | | 11/2005 | |
| KR | 10-2006-0122604 | | 11/2006 | |
| KR | 10-2013-0047779 | | 5/2013 | |
| KR | 10-1952784 | B | 2/2019 | |
| RU | 2208440 | C2 | 7/2003 | |
| RU | 2276157 | C2 | 5/2006 | |
| RU | 2308460 | C2 | 10/2007 | |
| WO | WO 02/04000 | A1 | 1/2002 | |
| WO | WO 2008/126905 | A1 | 10/2008 | |
| WO | WO 2009/021790 | A1 | 2/2009 | |
| WO | WO 2009/157409 | A1 | 12/2009 | |
| WO | WO-2011088941 | A1 * | 7/2011 | ............ A23L 2/68 |

OTHER PUBLICATIONS

Kankia H, Immunomodulatory effects of carbohydrates and advanced glycation end products, Biotechnology and Molecular Biology Reviews, vol. 10(1), pp. 1-11, Jan. 2015 (Year: 2015).*
Second Office Action received in Taiwan Patent Application No. 106126890 dated Dec. 12, 2018.
Kinoshita et al., "Exploratory Trial Concerning Activation of Human Natural Immunity by Continued Consumption of a Broccoli Extract Processed Food Product", Jpn Pharmacol Ther vol. 40 No. 6 2012, p. 489-495.
First Examination Report issued in the corresponding IN Patent application No. 201927006536, dated Dec. 27, 2019.
Examination Report No. 2 issued in AU application No. 2017310867, dated May 11, 2020.
Tomoda, et al "Characterization of Two Acidic Polysaccharides Having Immunological Activities from the Root of Panax ginseng", Biol. Pharm Bull. 16(1) 22-25 (1993) vol. 16, No. 1.
Notice of Reasons for Refusal issued in JP application No. 2016-156274 dated May 27, 2020 & its machine-generated English translation.
Saphala, D., et al., Purification of Innate Immunostimulant from Green Tea Using a Silkworm Muscle Contraction Assay, Drug Discoveries & Therapeutics 5(1):18-25, 2011.
Ishii, K., et al., Activation of the Silkworm Cytokine by Bacterial and Fungal Cell Wall Components via a Reactive Oxygen Species-Triggered Mechanism, Journal of Biological Chemistry 283(4):2185-91, 2008.
Ishii, K., et al., Insect Cytokine Paralytic Peptide (PP) Induces Cellular and Humoral Immune Responses in the Silkworm *Bombyx mori*, Journal of Biological Chemistry 285(37):28635-42, 2010.
Ishii, K., et al. Porphyromonas gingivalis Peptidoglycans Induce Excessive Activation of the Innate Immune System in Silkworm Larvae, et al., Journal of Biological Chemistry 285(43):33338-47, 2010.
Dhital, S., et al., Purification of Innate Immunostimulant From Green Tea Using a Silkworm Muscle Contraction Assay, Drug Discoveries & Therapeutics 5(1):18-25, 2011.
Fujiyuki, T., et al., Evaluation of Innate Immune Stimulating Activity of Polysaccharides Using a Silkworm (*Bombyx mori*) Muscle Contraction Assay, Drug Discoveries & Therapeutics 6(2):88-93, 2012.
Kinoshita, H., et al., Exploratory Trial Concerning Activation of Human Natural Immunity by Continued Consumption of a Broccoli Extract Processed Food Product, Japan Pharmacology and Therapeutics. 40(6):489-94, 2012.
Cheng, B.-H., et al., Structural Characterization and Immunomodulatory Effect of a Polysaccharide HCP-2 From Houttuynia cordata, Carbohydr. Polym. 103:244-9, 2014.
Wang, M. et al., Preparation, Preliminary Characterization and Immunostimulatory Activity of Polysaccharide Fractions from the Peduncles of Hovenia dulcis, Food Chemistry 138(1):41-7, 2013.
He, Y.-T., et al., Biological Activity and Structure of Plant Polysaccharides, Food Science 31(17):493-6, 2010.
Studies on Extraction, Purification, Bioactivity and Structure of Polysaccharides from Arietinum Hull, Nanjing Agricultural Univ., Master's Degree Abstract, Apr. 1, 2016.
International Search Report in connection with International Patent Application No. PCT/JP2017/029237 dated Oct. 24, 2017.
Written Opinion in connection with International Patent Application No. PCT/JP2017/029237 dated Oct. 24, 2017.
First Office Action in connection with Taiwan Patent Application No. 106126890 dated Aug. 2, 2018.
Examiner's Report issued in CA patent application No. 3033187, dated Feb. 13, 2020.
Extended Search Report issued in EP patent application No. 17839606.5, dated Mar. 10, 2020.
Examination Report in Australian Patent Application No. 2017310867 dated Nov. 12, 2019.
Notification of Reason for Refusal in Korean Patent Application No. 10-2018-7036771 dated Oct. 25, 2019.
Office Action in Russian Patent Application No. 2019105674 dated Sep. 20, 2019.
Office Action issued in CN application No. 201780035277.X, dated Jun. 22, 2020.
Examiner's Report for Canadian Patent Application No. 3033187, dated Sep. 9, 2020.
Examination Report for Australian Patent Application No. 2017310867, dated Oct. 9, 2020.
Final Rejection for Korean Patent Application No. 10-2018-7036771, dated Sep. 15, 2020.
Xu, Lishan, Jingjing Cao, and Wenrong Chen. "Structural characterization of a broccoli polysaccharide and evaluation of anti-cancer cell proliferation effects." Carbohydrate polymers 126 (2015): 179-184.
Office Action dated Dec. 17, 2020, issued in the corresponding Chinese Patent Application No. 201780035277.X.
Second Examination Report in the corresponding Indian Application No. 201927006536, dated Oct. 23, 2020.
Email communication between the Indian Representative and Japan Representative regarding the applicant amending the current pending claims for Indian Patent No. 201927006536, on Jan. 11, 2021.

* cited by examiner

POLYSACCHARIDE HAVING INNATE IMMUNITY STIMULATING ACTIVITY

TECHNICAL FIELD

The present invention relates to a polysaccharide having innate immune stimulating activity and an innate immune stimulant or food and drink comprising the polysaccharide.

BACKGROUND ART

Higher vertebrate animals such as humans have two types of immune mechanisms (immune systems): innate immunity and acquired immunity. The two immune mechanisms work in a coordinated manner to protect against infectious sources. In contrast, many other living organisms such as insects are devoid of acquired immunity and thus protect themselves from infectious sources only with innate immunity.

Innate immunity is a common defense mechanism against infections among living organisms. Innate immunity is non-specific and responds quickly, which enables it to function effectively against a variety of infectious sources. Non-specific innate immunity is considered to be more important than specific acquired immunity in higher vertebrate animals, including humans, because it provides early phase resistance against infections, prevention of cancers and lifestyle-related diseases, repair of tissues, and the like.

Innate immunity is a key host factor in the biological defense mechanism in the early phase of infections. Activation of innate immunity is considered to be effective to prevent and treat infectious diseases. As the importance of developing cancer drugs has become more important in recent years, the innate immune stimulating activity of polysaccharides derived from mushrooms, which also provide antitumor activity, has gathered attention.

The inventors have so far found that injection of innate immune-stimulants such as β-glucan derived from fungus or peptidoglycan derived from bacterium into silkworm muscle preparations induces an insect cytokine, which is a paralytic peptide that activates innate immunity along with muscle contraction (Patent Literature 1 and Non Patent Literatures 1 to 3). By measuring the body length change due to this muscle contraction, the inventors have established a simple screening system for innate immunity stimulants, which enabled them to identify innate immune stimulating activity in polysaccharides extracted from green tea and other sources (Non Patent Literatures 4 and 5).

Vegetables have been empirically known to be important for intake of necessary nutrients for human health maintenance, and also have been used worldwide as traditional medicinal plants. Vegetables could potentially contain innate immune stimulants, but no substances from vegetables have been identified so far that clearly stimulate innate immune function.

The inventors have found that a broccoli extract exhibits innate immune stimulating activity (Patent Literature 1). However, it has not been clarified which component in broccoli is directly responsible for the innate immune-stimulating activity. Also, it has not been clarified which portion (chemical structure) of the component (compound) has the innate immune stimulating activity.

Previously, only few attempts have been tried to purify active portions (chemical structures) for use as innate immune stimulants by decomposing chemical bonds of components (compounds) extracted from living organisms, including broccoli. In other words, an innate immune stimulant defined by a specific chemical structure that is effective for innate immune stimulation have almost not been prepared (synthesized) by using a component (compound) extracted from a living organism as a raw material.

CITATION LIST

Patent Literature

Patent Literature 1: International Publication No. WO2008/126905

Non-Patent Literature

Non Patent Literature 1: Activation of the silkworm cytokine by bacterial and fungal cell wall components via a reactive oxygen species-triggered mechanism. Ishii K, Hamamoto H, Kamimura M, Sekimizu K. J Biol Chem. 2008, 283(4), 2185-91.

Non Patent Literature 2: Insect cytokine paralytic peptide (PP) induces cellular and humoral immune responses in the silkworm *Bombyx mori*. Ishii K, Hamamoto H, Kamimura M, Nakamura Y, Noda H, Imamura K, Mita K, Sekimizu K. J Biol Chem. 2010, 285(37), 28635-42.

Non Patent Literature 3: *Porphyromonas gingivalis* peptidoglycans induce excessive activation of the innate immune system in silkworm larvae. Ishii K, Hamamoto H, Imamura K, Adachi T, Shoji M, Nakayama K, Sekimizu K. J Biol Chem. 2010, 285(43), 33338-47.

Non Patent Literature 4: Purification of innate immune stimulant from green tea using a silkworm muscle contraction assay. Dhital S, Hamamoto H, Urai M, Ishii K, Sekimizu K. Drug Discoveries & Therapeutics. 2011, 5(1), 18-15.

Non Patent Literature 5: Evaluation of innate immune stimulating activity of polysaccharides using a silkworm (*Bombyx mori*) muscle contraction assay. T. Fujiyuki, H. Hamamoto, K. Ishii, M. Urai, K. Kataoka, T. Takeda, S. Shibata and K. Sekimizu. Drug Discoveries & Therapeutics, 6(2), 88-93, 2012.

SUMMARY OF INVENTION

Technical Problem to be Solved

In view of the background art described above, the present invention has been made to provide a new substance having innate immune stimulating activity.

Solution to Problem

The inventors intensively studied to solve the problem using the silkworm muscle contraction assay established by the inventors, and successfully purified an innate immune stimulating substance from a broccoli extract. The inventors further analyzed the structure of the substance and studied it for the structure responsible for the immune stimulating activity.

As a result, the inventors have identified new polysaccharides having a previously unknown structure from purified broccoli extract, which have innate immune-stimulating activity.

Further, the inventors have revealed that a polygalacturonic acid chain, which is a constituent of the polysaccharide, has an important role for its innate immune-stimulating activity, thereby achieving the present invention.

Thus, the present invention provides a polysaccharide having innate immune stimulating activity, comprising:

as constituent sugars, 25 to 50 parts by mole of galacturonic acid, 15 to 50 parts by mole of galactose, 0 to 7 parts by mole of glucose, 0 to 30 parts by mole of arabinose, 0 to 6 parts by mole of xylose, and 3 to 15 parts by mole of rhamnose; and as a main chain, a polygalacturonic acid chain comprising α-1,4-linked galacturonic acid.

The present invention also provides an innate immune stimulant comprising the above polysaccharide as an active component.

The present invention further provides a food or drink comprising the above polysaccharide.

Effects of Invention

The present invention provides a polysaccharide of a new chemical structure having innate immune stimulating activity.

The present invention also provides an innate immune stimulant comprising the polysaccharide as an active component as well as a food or drink comprising the polysaccharide having innate immune stimulating activity.

The polysaccharide of the present invention is extremely safe with no side effects. Moreover, the polysaccharide can be easily processed into various dosage forms and easily added to foods and drinks. Therefore, the polysaccharide effectively and safely stimulates innate immunity in the form of the innate immune stimulant or functional food.

DETAILED DESCRIPTION OF THE PREFERRED EMBODIMENT

Figure 1:
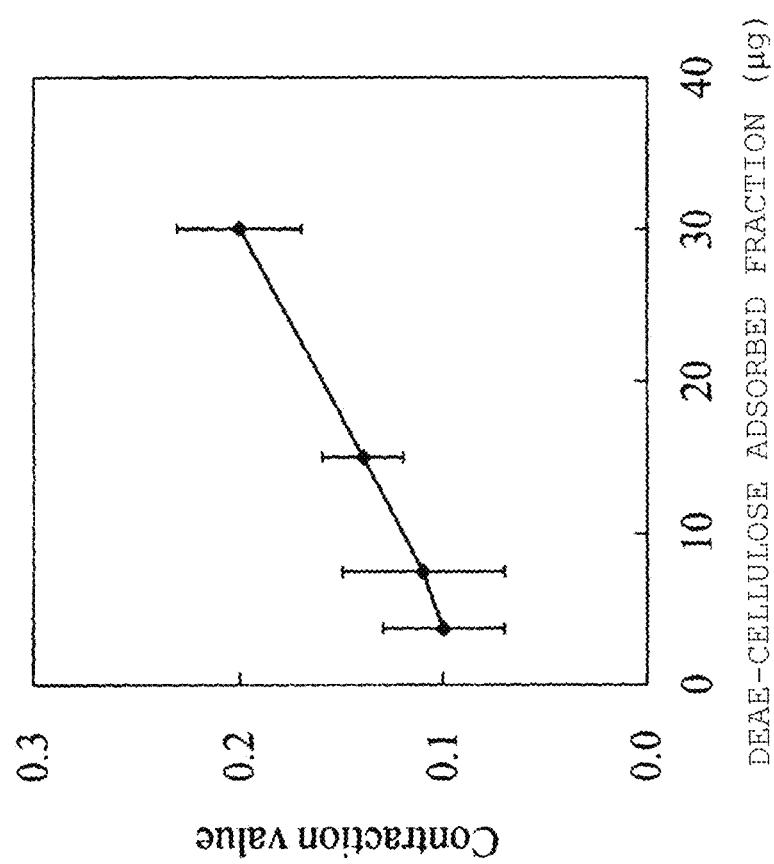
FIG. 1 is a graph showing the specific activity (C value) measurement obtained by injection of a DEAE-cellulose adsorbed fraction into silkworms.

The present invention will be further explained hereinafter, but the present invention is not limited to the specific embodiments described below. The present invention can be modified arbitrarily within the technical scope of the invention.

<Polysaccharide>

The polysaccharide of the present invention has innate immune stimulating activity and is characterized by comprising:

25 to 50 parts by mole of galacturonic acid, 15 to 50 parts by mole of galactose, 0 to 7 parts by mole of glucose, 0 to 30 parts by mole of arabinose, 0 to 6 parts by mole of xylose, and 3 to 15 parts by mole of rhamnose as constituent sugars; and a polygalacturonic acid chain having α-1,4-linked galacturonic acid as a main chain.

It is essential for the polysaccharide of the present invention to comprise 25 to 50 parts by mole of galacturonic acid, 15 to 50 parts by mole of galactose, 0 to 7 parts by mole of glucose, 0 to 30 parts by mole of arabinose, 0 to 6 parts by mole of xylose, and 3 to 15 parts by mole of rhamnose as constituent sugars.

Preferably, the polysaccharide comprises 25 to 45 parts by mole of galacturonic acid, 20 to 50 parts by mole of galactose, 1 to 7 parts by mole of glucose, 0 to 20 parts by mole of arabinose, 0 to 6 parts by mole of xylose, and 4 to 14 parts by mole of rhamnose as constituent sugars.

More preferably, the polysaccharide comprises 25 to 40 parts by mole of galacturonic acid, 30 to 50 parts by mole of galactose, 3 to 7 parts by mole of glucose, 0 to 10 parts by mole of arabinose, 0 to 5 parts by mole of xylose, and 5 to 13 parts by mole of rhamnose as constituent sugars.

Particularly preferably, the polysaccharide comprises 30 to 40 parts by mole of galacturonic acid, 35 to 45 parts by mole of galactose, 5 to 6 parts by mole of glucose, 0 to 5 parts by mole of arabinose, 0 to 5 parts by mole of xylose, and 6 to 12 parts by mole of rhamnose as constituent sugars.

The polysaccharide of the present invention may comprise a monosaccharide other than the above monosaccharides, as long as the effect of the present invention is not impaired.

The polysaccharide of the present invention comprises a polygalacturonic acid chain having α-1,4-linked galacturonic acid as a main chain. The polygalacturonic acid chain may comprise a monosaccharide other than galacturonic acid as long as the effect of the present invention is not impaired.

Examples of the "monosaccharide other than galacturonic acid" include rhamnose.

The proportion of the galacturonic acid (units) in the "polygalacturonic acid chain" is preferably from 20 mol % to 99 mol %, more preferably 30 mol % to 97 mol %, and particularly preferably 40 mol % to 95 mol % with respect to the total amount of the "polygalacturonic acid chain".

If the proportion of the linked galacturonic acid (units) in the main chain of "polygalacturonic acid chain" is too low, the innate immune stimulating activity of the polysaccharide may decrease. On the contrary, if the proportion is too high, the polysaccharide is difficult to obtain.

The polysaccharide of the present invention has a new structure in view of its not containing galacturonic acid methyl ester which makes the polysaccharide of the present invention different from pectins. Further, the "polysaccharide of the present invention" is a new substance as being a substance purified from a natural product having a chemical structure with innate immune stimulating activity.

The polysaccharide of the present invention was found by purification of a broccoli extract, which is composed of many number of components. It is not easy to identify a component having the innate immune stimulating activity among these large number of components.

The inventors repeatedly measured the innate immune stimulating activity of each of the "large number of components of the broccoli extract" separately by using the simple and less-morally concerning silkworm muscle contraction assay, and finally achieved the present invention.

Further, the inventors decomposed and purified the chemical structures (units) from the components, which were further analyzed by the silkworm muscle contraction assay repeatedly again, and finally achieved the present invention by discovering a chemical structure (unit) having innate immune stimulating activity from the many chemical structures (units).

The polysaccharide of the present invention may be derived from natural source obtained by purification, decomposition and the like from a natural product, obtained by chemical modification of natural product as a raw material, or completely synthesized.

<Innate Immune Stimulant>

The innate immune stimulant of the present invention is characterized by comprising the above polysaccharide as an active component.

The polysaccharide contained as an active component in the innate immune stimulant of the present invention may be naturally-derived or synthesized.

The ratio of content volume of the polysaccharide, an active component of the innate immune stimulant of the present invention, relative to the total amount of the innate immune stimulant is not particularly limited, and may be appropriately determined depending on the purpose. Preferably, with respect to 100 parts mass of the total innate immune stimulant, the total content of polysaccharide is preferably 0.01 to 100 parts mass, more preferably 0.1 to 99 parts mass, particularly preferably 1 to 95 parts mass, and even more preferably 10 to 90 parts mass.

The innate immune stimulant of the present invention can includes "other components" in addition to the active component of polysaccharide.

The "other components" are not particularly limited and can be selected appropriately depending on the purpose as long as the effect of the present invention is not impaired. Examples of the other components include pharmaceutically acceptable carriers.

The carrier is not particularly limited, and can be selected appropriately depending on, for example, the dosage form described below. The content of the "other components" in the innate immune stimulant is not particularly limited either and can be selected appropriately depending on the purpose.

The dosage form of the innate immune stimulant of the present invention is not particularly limited and can be selected appropriately depending on, for example, the desired administration method described below.

Specific examples of the dosage form include an oral solid formulation (such as a pill, coated pill, granule, powder, or capsule), an oral liquid formulation (such as a liquid for internal use, a syrup, or an elixir), an injectable (such as a solution or suspension), an ointment, a patch, a gel, a cream, a powder for external use, a spray, and an inhalant.

The oral solid formulation can be produced according to the common method by adding an excipient, and if necessary, additives such as a binder, a disintegrant, a lubricant, a colorant, and a flavoring agent to the active component described above.

Examples of the excipient include lactose, saccharose, sodium chloride, glucose, starch, calcium carbonate, kaolin, microcrystalline cellulose, and silicic acid.

Examples of the binder include water, ethanol, propanol, simple syrup, a glucose solution, a starch solution, a gelatin solution, carboxymethyl cellulose, hydroxypropyl cellulose, hydroxypropyl starch, methyl cellulose, ethyl cellulose, shellac, calcium phosphate, and polyvinylpyrrolidone.

Examples of the disintegrant include dry starch, sodium alginate, powdered agar, sodium hydrogen carbonate, calcium carbonate, sodium lauryl sulfate, monoglyceride stearate, and lactose.

Examples of the lubricant include purified talc, stearic acid salts, borax, and polyethylene glycol.

Examples of the colorant include titanium oxide and iron oxide.

Example of the flavoring agent include saccharose, orange peel, citric acid, and tartaric acid.

The oral liquid formulation can be produced according to common methods, for example, by adding additives such as a flavoring agent, a buffer, and a stabilizer to the active component described above.

Examples of the flavoring agent include saccharose, orange peel, citric acid, and tartaric acid. Examples of the buffer include sodium citrate. Examples of the stabilizer include tragacanth, gum arabic, and gelatin.

The injectable can be produced according to the common method for subcutaneous injection, intramuscular injection, or intravenous injection, for example, by adding a pH adjuster, a buffer, a stabilizer, a tonicity agent, a local anesthetic, etc. to the active component described above.

Examples of the pH adjuster and the buffer include sodium citrate, sodium acetate, and sodium phosphate. Examples of the stabilizer include sodium pyrosulfite, EDTA, thioglycolic acid, and thiolactic acid. Examples of the tonicity agent include sodium chloride and glucose. Examples of the local anesthetic include procaine hydrochloride and lidocaine hydrochloride.

The ointment can be produced, for example, by adding a base, a stabilizer, a wetting agent, a preservative etc. which are all known to the active component described above and mixing them according to the common method.

Examples of the base include liquid paraffin, white petrolatum, white beeswax, octyldodecyl alcohol, and paraffin. Examples of the preservative include methyl p-oxybenzoate, ethyl p-oxybenzoate, and propyl p-oxybenzoate.

The patch can be produced, for example, by applying the ointment in the form of a cream, a gel, or a paste to a known support using a common method. Examples of the support include: a woven fabric or non-woven fabric made of cotton, staple fiber, or chemical fiber; a film of soft vinyl chloride, polyethylene, polyurethane, and the like; and a foam sheet.

The innate immune stimulant of the present invention can be used by being administered, for example, into an individual requiring stimulation of the innate immune mechanism (such as an individual requiring health maintenance or recovery from exhaustion, an individual requiring prevention or treatment of a cancer or lifestyle-related disease, or an individual infected with a bacterium, a fungus, a virus, and the like).

The animal to which the innate immune stimulant of the present invention can be administered is not particularly limited, and examples include human; mice; rats; monkeys; horses; livestock, such as cows, pigs, goats, and chickens; and pet animals, such as cats and dogs.

The administration method of the innate immune stimulant is not particularly limited and can be selected appropriately depending on, for example, the dosage form of the innate immune stimulant. Examples include oral administration, intraperitoneal administration, injection into the blood, and infusion into the intestine.

The dose of the innate immune stimulant is not particularly limited and can be selected appropriately depending on the age and weight of an individual to be administered, the desired extent of the effect, and the like. For example, the dose per day for an adult human is preferably 1 mg to 30 g, more preferably 10 mg to 10 g, and particularly preferably 100 mg to 3 g of the total amount of the polysaccharide as an active component.

The timing of administration of the innate immune stimulant is not particularly limited either and can be selected appropriately depending on the purpose. For example, the innate immune stimulant may be prophylactically or therapeutically administered.

<Food or Drink>

The food or drink of the present invention is characterized by comprising the above-described polysaccharide or the above-described innate immune stimulant of the present invention.

The food or drink of the present invention has innate immune stimulating activity.

The content of the polysaccharide or the innate immune stimulant in the food or drink comprising the polysaccharide or the innate immune stimulant (hereinafter, abbreviated as "food or drink of the present invention") is not particularly limited and can be selected appropriately depending on the purpose or the form (type) of the food or drink. The content of the total innate immune stimulant is preferably 0.001 to 100 parts mass, more preferably 0.01 to 100 parts mass, and particularly preferably 0.1 to 100 parts mass with respect to 100 parts mass of the total food or drink.

A polysaccharide or an innate immune stimulant may be used alone, or two or more polysaccharides or innate immune stimulants may be used in combination. When two or more polysaccharides or innate immune stimulants are used in combination, the ratio of the content of each substance in the food or drink is not particularly limited and can be selected appropriately depending on the purpose.

The food or drink of the present invention can further comprise "other components" in addition to the polysaccharide or the innate immune stimulant of the present invention.

The "other components" in the food or drink of the present invention having such innate immune stimulating activity are not particularly limited and can be selected appropriately depending on the purpose as long as the effect of the present invention is not impaired. Examples of the "other components" include various food ingredients. The content of the "other components" is not particularly limited and can be selected appropriately depending on the purpose.

The type of the food or drink is not particularly limited and can be selected appropriately depending on the purpose. Examples of the food or drink include: confectionery such as jellies, candies, chocolates, and biscuits; tasty drinks such as green tea, black tea, coffee, and refreshing beverages; dairy products such as fermented milk, yogurts, and ice creams; processed vegetable or fruit products, such as vegetable beverages, fruit beverages, and jams; liquid foods, such as soups; processed grain products, such as breads and noodles; and various seasonings.

The method for producing these foods or drinks is not particularly limited. The foods or drinks can be produced appropriately according to a common method for producing various foods or drinks.

The food or drink may be produced as an oral solid formulation such as a pill, granule, or capsule or as an oral liquid formulation such as a liquid for internal use or a syrup. The method for producing the oral solid formulation or oral liquid formulation is not particularly limited and can be selected appropriately depending on the purpose. For example, the oral solid formulation or oral liquid formulation can be produced according to the above-described method for producing a drug in the form of an oral solid formulation or oral liquid formulation.

The food or drink is considered particularly useful as a functional or health food or drink and the like for stimulating the innate immune mechanism.

When the polysaccharide or innate immune stimulant of the present invention is used for production of a food or drink, the production method can be carried out by a method well-known to persons skilled in the art. Persons skilled in the art will be able to make a food or drink of interest by appropriately combining various steps such as a step of mixing the polysaccharide of the present invention with other components, a forming step, a sterilization step, a fermentation step, a baking step, a drying step, a cooling step, a granulation step, and a packaging step.

EXAMPLES

Hereinafter, the present invention will be described more specifically using Examples, Comparative examples, and Test examples. The present invention is not limited to these Examples as long as it will not depart from the gist of the present invention.

<Hot Water Extraction>

Various vegetables were cut, to which water was added, and then autoclaved at 121° C. for 20 minutes. The vegetables were left to cool, and then centrifuged at 8000 rpm for 10 minutes, to obtain the resulting supernatant as a "hot water extract".

<Silkworm Muscle Contraction Assay>

The sample was dissolved in a buffer, which of 100 μL was injected into a silkworm muscle preparation to measure muscle contraction. The innate immune stimulating ability was determined to be positive if the sample gave a specific activity or C value (contraction value) of 0.15 or more, which was calculated by dividing the difference in the muscle preparation length between before and after injection by the muscle preparation length before injection.

<Purification of DEAE-Cellulose Column Adsorbed Fraction>

A hot water broccoli extract was subjected to ethanol precipitation. The hot water extraction was conducted in accordance with the method described in Patent Literature 1. The obtained precipitate was dissolved in Milli-Q water, which was subjected to dialysis against the Milli-Q water, and freeze dried. The freeze-dried product was subjected to DEAE-cellulose column chromatography, and each of the resulting fractions was measured for the amount of reduced sugars by phenol-sulfuric acid method. The peak fractions containing eluted sugars were collected, subjected to dialysis, and freeze dried.

<Structure Analysis of DEAE-Cellulose Column Adsorbed Fraction>

[1. Monosaccharide Composition Analysis]

The DEAE-cellulose column adsorbed fraction was hydrolyzed with trifluoroacetic acid. The hydrolysate was labelled with aminobenzoic acid ethyl ester, which was subjected to HPLC analysis using an ODS column. A sample prepared by mixing following standard monosaccharides was analyzed in the same manner, and a retention time was compared: L-arabinose (Ara), L-fucose (Fuc), D-galactose (Gal), D-glucose (Glc), D-mannose (Man), L-rhamnose (Rha), D-ribose (Rib), D-xylose (Xyl), D-galacturonic acid (GalA), D-glucuronic acid (GlcA), N-acetyl-D-galactosamine (GalNAc), N-acetyl-D-glucosamine (GlcNAc), and N-acetyl-D-mannosamine (ManNAc).

[2. NMR Analysis]

27 mg of the DEAE-cellulose-column adsorbed fraction was dissolved in deuterated water (D20) at 40° C., which was subjected to $^1$H NMR analysis, $^{13}$C NMR analysis, DQF-COSY analysis, HMQC analysis, HMBC analysis, and TOCSY analysis.

[3. Methylation Analysis]

The DEAE-cellulose column adsorbed fraction was methylated, and then hydrolyzed with trifluoroacetic acid. The hydrolysate was acetylated to give alditol acetate, which was analyzed by GCMS.

<Selective Decomposition of DEAE-Cellulose Column Adsorbed Fraction>

[1. Selective Decomposition of Arabinose by Oxalic Acid Hydrolysis]

The DEAE-cellulose column adsorbed fraction was hydrolyzed by oxalic acid, neutralized, dialyzed, and then freeze dried.

[2. Decomposition of Polygalacturonic Acid Chain by Pectinase]

The DEAE-cellulose column adsorbed fraction was treated with pectinase (Sigma-Aldrich Co., LLC.). After heating to deactivate the enzyme, the fraction was subjected to Bio-gel P4 gel filtration column chromatography. Each of the resulting fractions was measured for an amount of reduced sugars by phenol-sulfuric acid method. The Bio-gel P4 gel filtration column had 1150 nm×15 mm 0, and 0.2 M acetic acid was used as an eluent. The peak fractions containing eluted sugars were collected and dried under reduced pressure.

Example 1

[Screening for Vegetables which contains Innate Immune Stimulating Substance]

Hot water extracts of 17 kinds of vegetables (broccoli, cabbage, carrot, pepper, *Siraitia grosvenorii* fruit, spinach, garlic, pumpkin, ginger, cherry tomato, radish, pea sprout, parsley, cucumber, eggplant, cibol, and napa cabbage) were compared for their innate immune stimulating potential by using silkworm muscle contraction assay.

TABLE 1

| Vegetable | Specific activity (C value) (units/mg) |
|---|---|
| Broccoli | 7 |
| Cabbage | <0.4 |
| Carrot | 0.6 |
| Pepper | 0.3 |
| *Siraitia grosvenorii* fruit | 0.6 |
| Spinach | <0.2 |
| Garlic | 0.0 |
| Pumpkin | <0.1 |
| Ginger | <0.3 |
| Cherry tomato | 0.5 |
| Radish | 0.2 |
| Pea sprout | <0.2 |
| Parsley | 0.7 |
| Cucumber | 0.8 |
| Eggplant | 0.5 |
| Cibol | 1 |
| Napa cabbage | 0.3 |

Table 1 shows the measured specific activity values (C values) for the hot water extracts of 17 vegetables obtained by the silkworm muscle contraction assay. A hot water extract that exhibited a specific activity (C value) of 0.15 or more is determined to have innate immune stimulating ability. The results of Table 1 indicates that the hot water extract of broccoli exhibited a strong innate immune stimulating ability.

Example 2

[Purification of Innate Immune stimulating Substance from Broccoli]

An innate immune stimulating substance was purified from a hot water extract of broccoli utilizing an index of silkworm muscle contraction activity. Table 2 shows the results of specific activity values (C values) at different stages of purification.

TABLE 2

| Fraction | Total activity (units) | Amount (mg) | Specific activity (C value) (units/mg) |
|---|---|---|---|
| Hot water extraction | 50,000 | 800 | 63 |
| Ethanol extraction | 11,000 | 250 | 44 |
| DEAE-cellulose column adsorbed fraction | 13,000 | 100 | 130 |

As a result of ethanol precipitation of the hot water extract, active component was collected in the precipitate (Table 2), which suggested that the active substance could be a polysaccharide. Subsequent DEAE-cellulose column chromatography gave a homogeneous sugar peak elution by NaCl gradient. The fraction of this peak showed an increased specific activity (Table 2).

Then, this fraction was examined for dose responsivity. The result is shown in FIG. 1. In FIG. 1, the ordinate represents the specific activity (C value), and the abscissa represents the amount of the DEAE-cellulose column adsorbed fraction (μg).

This fraction exhibited a specific activity of 67 unit/mg (FIG. 1), where an activity corresponding to a C value (contraction value) of 0.15 is set as 1 unit. Further analysis were conducted in the Examples with using this fraction as a purified fraction.

Example 3

[Structure Analysis of DEAE-Cellulose Column Adsorbed Fraction]

Figure 2:
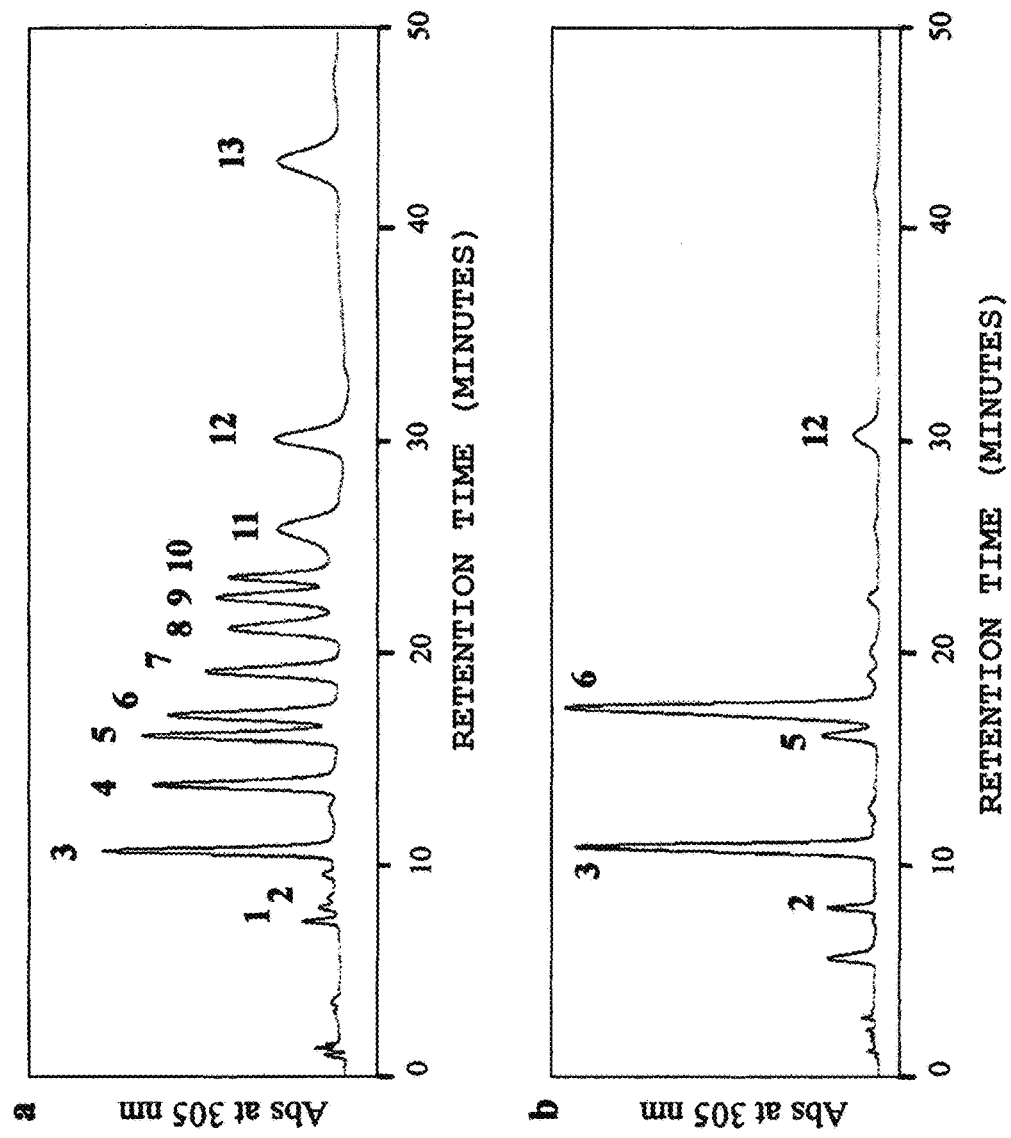
FIG. 2(a) is a spectrum of HPLC analysis for a standard sample
FIG. 2(b) is a spectrum of HPLC analysis for a hydrolysate of a DEAE-cellulose adsorbed fraction.

In order to reveal the monosaccharide composition of the obtained DEAE-cellulose column adsorbed fraction, a trifluoroacetic acid hydrolysate of the fraction was analyzed by HPLC. The analysis result is shown in FIG. 2. FIG. 2*a* shows a result of HPLC analysis of a standard sample, and FIG. 2*b* shows a result of HPLC analysis of the DEAE-cellulose column adsorbed fraction.

In FIG. 2, the numeral 1 represents D-glucuronic acid, the numeral 2 represents D-galacturonic acid, the numeral 3 represents D-galactose, the numeral 4 represents D-mannose, the numeral 5 represents D-glucose, the numeral 6 represents L-arabinose, the numeral 7 represents D-ribose, the numeral 8 represents N-acetyl-D-mannosamine, the numeral 9 represents D-xylose, the numeral 10 represents N-acetyl-D-glucosamine, the numeral 11 represents L-fucose, the numeral 12 represents L-rhamnose, and the numeral 13 represents N-acetyl-D-galactosamine.

The results of FIG. 2 show that galacturonic acid (GalA), galactose (Gal), glucose (Glc), arabinose (Ara), and rhamnose (Rha) were detected, and their molar ratio as expressed by GalA:Gal:Glc:Ara:Rha was 12.4:4.9:1.0:7.3:1.2.

Then, the sugar chain structure was analyzed by NMR. The results are shown in FIG. 3.

Figure 3:
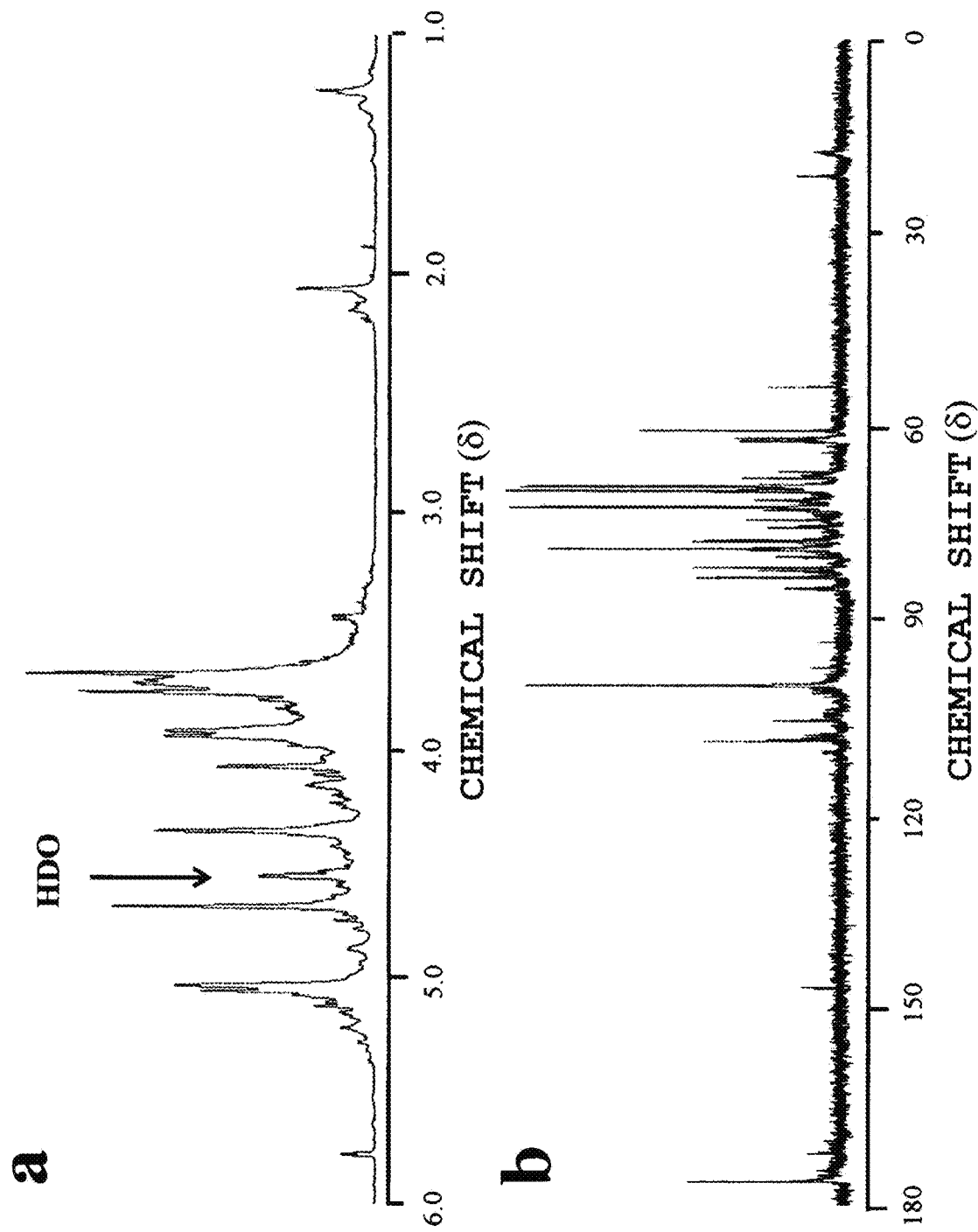
FIG. 3 shows (a) a $^1$H NMR spectrum at 500 MHz and (b) a $^{13}$C NMR spectrum at 125 MHz for a DEAE-cellulose adsorbed fraction.

The result of 1D NMR analysis showed patterns characteristic to sugars, but no signals characteristic to proteins and lipids (FIG. 3).

Then, various modes of 2D NMR analysis were carried out, and the detected signals were assigned. The results are collectively shown in Table 3.

TABLE 3

| Glycosyl residue | H-1 C-1 | H-2 C-2 | H-3 C-3 | H-4 C-4 | H-5 C-5 | H-6 C-6 |
|---|---|---|---|---|---|---|
| →4)-α-GalpA-(1→ | 5.07 | 3.76 | 3.98 | 4.41 | 4.73 | — |
|  | 99.8 | 69.1 | 69.8 | 78.8 | 72.2 | 176.2 |
| →5)-α-Araf(1→ | 5.09 | 4.13 | 4.02 | 4.21 | 3.84 | — |
|  | 108.3 |  |  |  | 61.7 | — |

The signal intensity of a main constituent GalA (galacturonic acid) was strong, which evidenced the formation of an α-1,4-linked polygalacturonic acid chain. Ara (arabinose) was contained in the second largest amount, and a part of the signal was able to be assigned to Ara. The chemical shift value suggested that Ara was α-1,5 linked. The other minor sugar residues detected in the monosaccharide composition analysis gave low-intensity signals, and thus not all of the signals were assigned.

Figure 4:
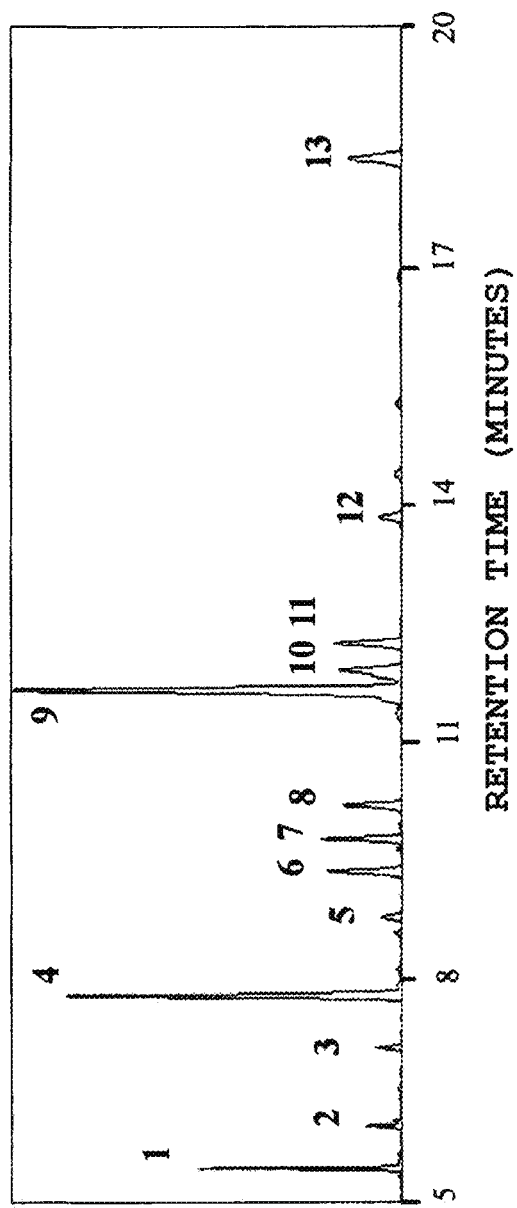
FIG. 4 is a spectrum of methylation analysis of a DEAE-cellulose adsorbed fraction against an alditol acetate derivative.

Therefore, a methylation analysis was employed in an attempt to determine the position of sugar linkage. The result is shown in FIG. 4. In FIG. 4, the numeral 1 represents T-Araf, the numeral 2 represents T-Rhap, the numeral 3 represents 3-Araf, the numeral 4 represents 5-Araf, the numeral 5 represents T-Glcp, the numeral 6 represents T-Galp, the numeral 7 represents 3,5-Araf, the numeral 8 represents 2,4-Rhap, the numeral 9 represents 4-GalpA, the numeral 10 represents 4-Galp, the numeral 11 represents 3-Galp, the numeral 12 represents 6-Galp, and the numeral 13 represents 3,6-Galp.

As shown in FIG. 4, peaks attributed to 13 types of partially methylated alditol acetate were detected. The sugar type and the linkage position were determined from the retention time and MS fragmentation pattern of each peak, which results are collectively shown in Table 4.

In Table 4, for example, "T-Araf" represents non-reducing terminal arabinose, "3-Galp" represents 3-linked galactose, and "3,5-Araf" represents 3,5-linked arabinose.

TABLE 4

| Peak | Linkage | mol % |
|---|---|---|
| 1 | T-Araf | 5.7 |
| 2 | T-Rhap | 1.3 |
| 3 | 3-Araf | 1.0 |
| 4 | 5-Araf | 16 |
| 5 | T-Glcp | 3.7 |
| 6 | T-Galp | 3.6 |
| 7 | 3,5-Araf | 4.4 |
| 8 | 2,4-Rhap | 3.2 |
| 9 | 4-GalpA | 46 |
| 10 | 4-Galp | 5.1 |
| 11 | 3-Galp | 3.7 |
| 12 | 6-Galp | 1.5 |
| 13 | 3,6-Galp | 4.5 |

In the methylation analysis, 1-44 linked galacturonic acid (GalA) and 1-45 linked arabinose (Ara) were detected as main constituents, which supported the results of the NMR analysis. Further, the linkage position was determined for the other minor sugar residues detected in the monosaccharide composition analysis.

Example 4

[Structure Required for Innate Immune stimulating Potential in DEAE-Cellulose Column Adsorbed Fraction]

To determine the structure required for the innate immune stimulating ability in the DEAE-cellulose column adsorbed fraction, the main constituents of arabinose and galacturonic acid were selectively decomposed to prepare a structurally modified product. The innate immune stimulating potential of the product were evaluated by silkworm muscle contraction analysis. The results are shown in Table 5.

TABLE 5

| Sample | | Sugar composition (mol %) | | | | | | Activity (units) |
|---|---|---|---|---|---|---|---|---|
| | | GalA | Gal | Glc | Ara | Xyl | Rha | |
| Purified product from broccoli extract | | 46 | 18 | 3.7 | 27 | ND | 4.5 | 630 |
| Oxalic acid hydrolysis | | 30 | 45 | 5.5 | 3.2 | 3.6 | 12 | 670< |
| Pectinase | Peak 1 | 23 | 22 | 5.0 | 28 | 5.0 | 18 | 370 |
| | Peak 2 | 24 | 24 | 6.0 | 17 | 5.5 | 24 | 240 |
| | Peak 3 | ND | 36 | 5.7 | 47 | ND | 12 | <160 |
| | Peak 4 | 100 | ND | ND | ND | ND | ND | <160 |

Firstly, selective decomposition and removal of arabinose (Ara) was conducted by oxalic acid hydrolysis, which was analyzed for the monosaccharide composition and showed a significant decrease in the Ara content (Table 5).

Further, the oxalic acid hydrolysate was dissolved in deuterated water (D20) at 70° C., and the solution was subjected to NMR analysis. The result is shown in FIG. 5.

Figure 5:
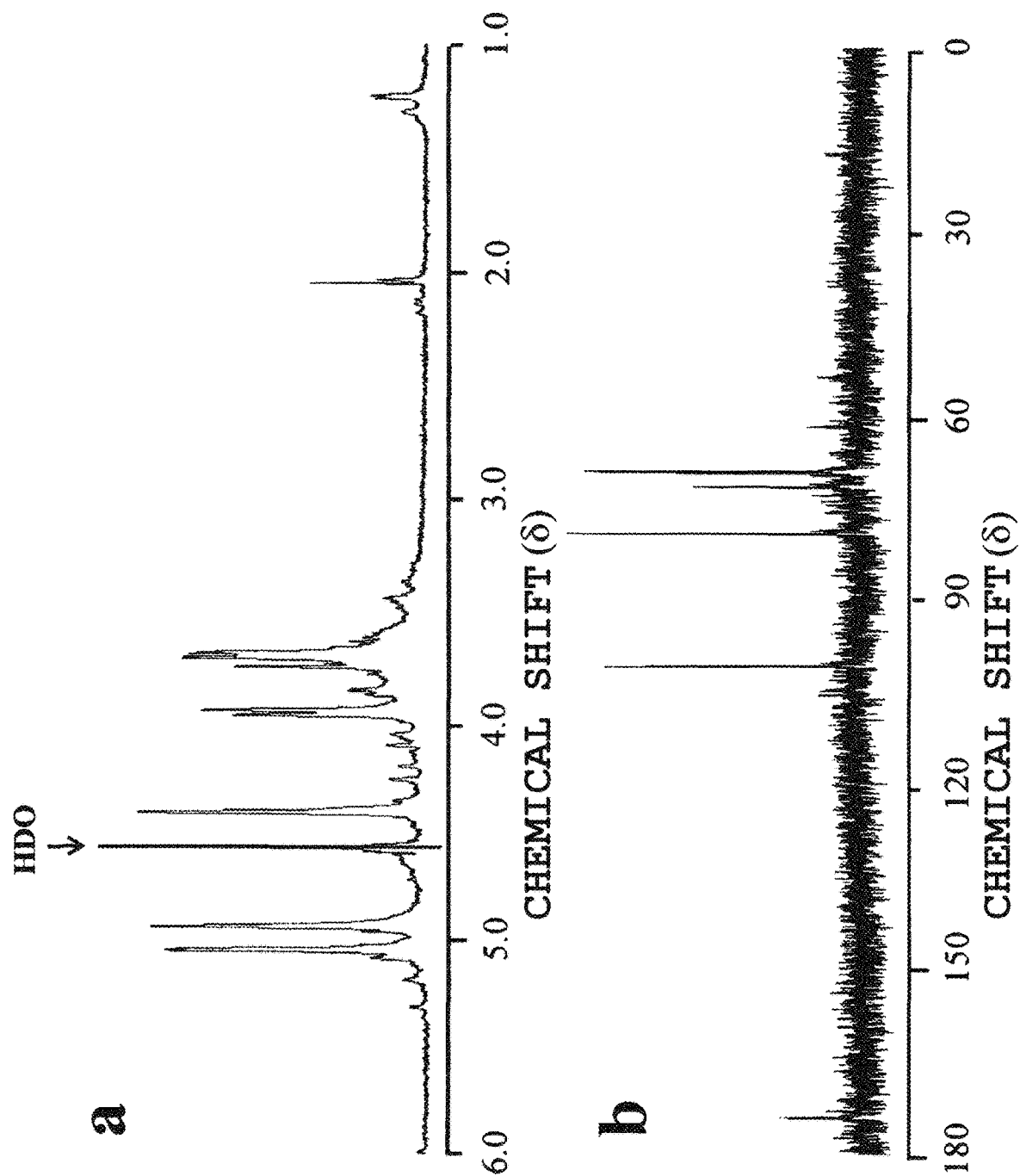
FIG. 5 shows (a) a $^1$H NMR spectrum at 500 MHz and (b) a $^{13}$C NMR spectrum at 125 MHz for an oxalic acid hydrolysis product.

The result of 1D NMR analysis indicates that the arabinose signal disappeared (FIG. 5). This sample (oxalic acid hydrolysis product) was subjected to silkworm muscle contraction assay, which showed that the innate immune stimulating ability was not lost (Table 5).

Figure 6:
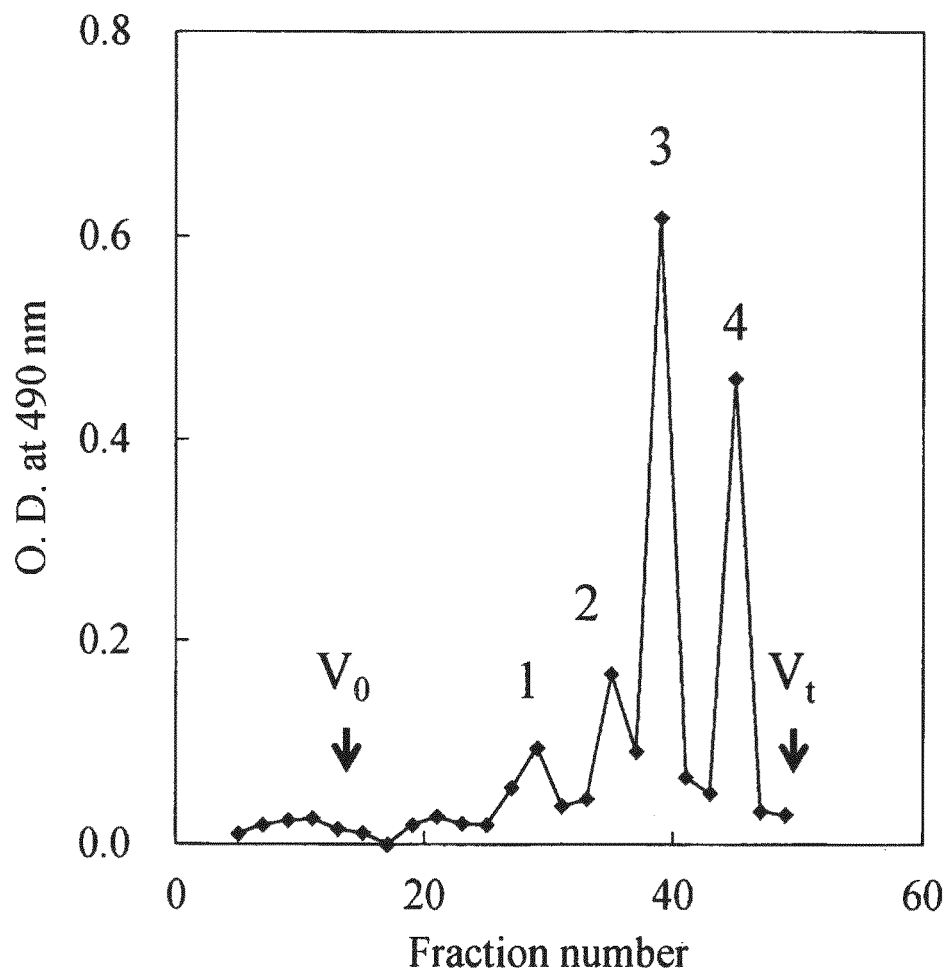
FIG. 6 is a graph of gel filtration chromatography fractionation of a pectinase-treated product.

Then, polygalacturonic acid was decomposed by pectinase treatment. The decomposed product was fractionated by Bio-gel P4 gel filtration column chromatography. The result of the fractionation is shown in FIG. 6. The numerals 1 to 4 in FIG. 6 correspond to "Peak 1" to "Peak 4" in Table 5, respectively.

As shown in FIG. 6, four peaks were detected. Each peak was analyzed for monosaccharide composition (Table 5), which showed that GalA, Gal, Glc, Ara, Rha, and Xyl were detected from Peaks 1 and 2. From Peak 3, GalA was not detected, but Gal, Glc, Ara, Rha, and Xyl were detected. From Peak 4, GalA monomer released by the pectinase treatment was detected. Each peak was subjected to silkworm muscle contraction assay (Table 5), which showed that the innate immune stimulating ability deteriorated with decreasing molecular weight and that the activity was not detected from Peak 3 or Peak 4.

<Summary and Discussion of Examples>

As a result of screening hot water extracts of 17 kinds of vegetables for an innate immune stimulating substance by using silkworm muscle contraction assay, high activity was observed for broccoli. In the Examples, a DEAE-cellulose column adsorbed fraction having innate immune stimulating potential was purified from broccoli.

The DEAE-cellulose column adsorbed fraction was subjected to structural analysis, the result of which suggested that the fraction was an acidic polysaccharide containing GalA, Gal, Glc, Ara, and Rha and having a main structure made up of an α-1,4-linked polygalacturonic acid chain as a main chain and an α-1,5-linked arabinan chain as a side chain.

The above result led to the inference that the DEAE-cellulose column adsorbed fraction is a type of pectin which is a plant cell wall component. However, as a result of the NMR analysis, almost no signal attributed to GalA methyl ester generally contained in pectin was detected. This suggested that the structure of the fraction was different from those of pectins previously reported.

To determine the structure required for the innate immune stimulating potential in the DEAE-cellulose column adsorbed fraction, arabinose and galacturonic acid which were the main constituents were selectively decomposed. As a result of decomposition of the polygalacturonic acid chain by pectinase treatment, the innate immune stimulating potential deteriorated with decreasing molecular weight and disappeared.

Figure 7:
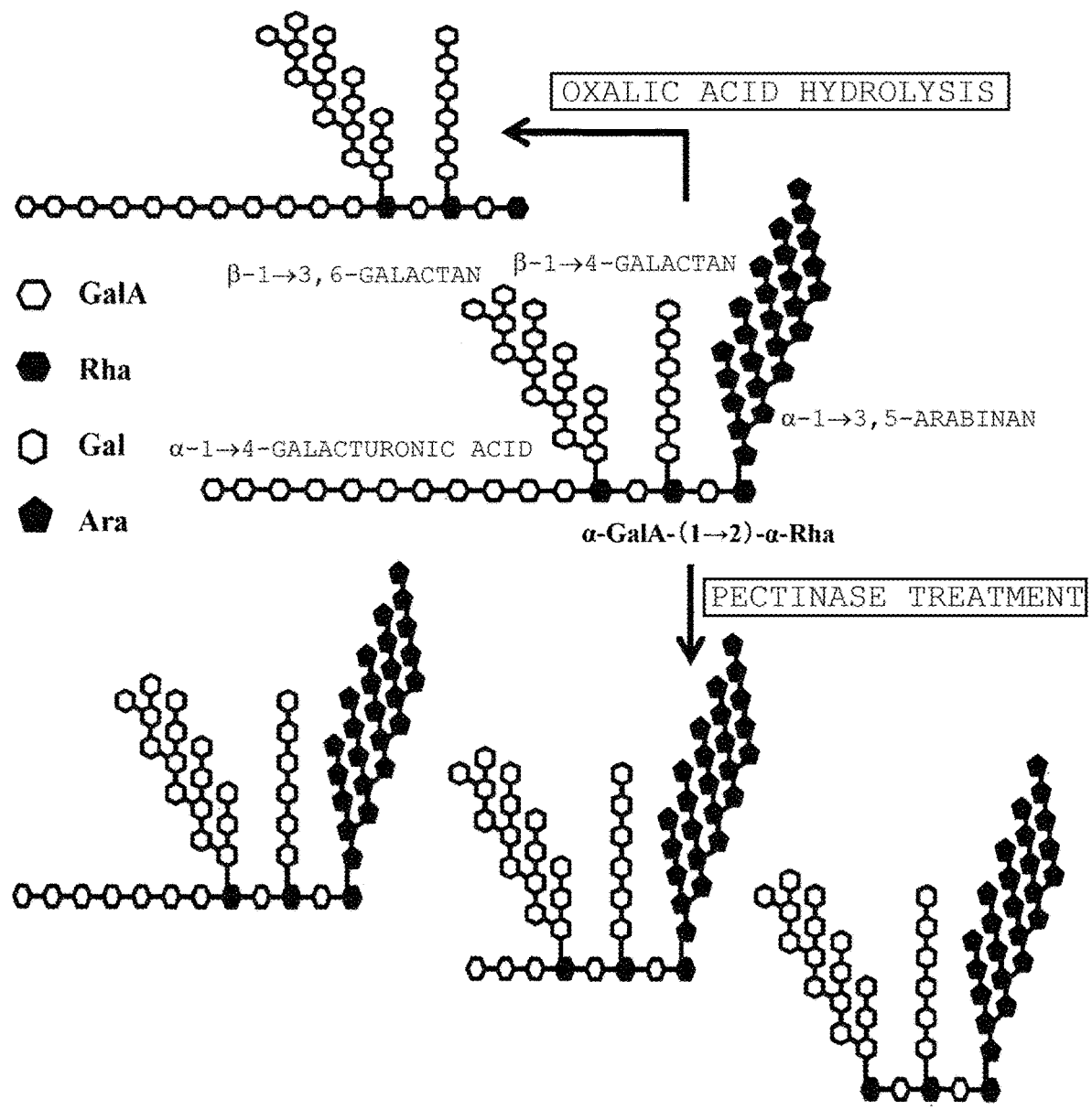
FIG. 7 is a schematic diagram illustrating exemplary chemical structures of the polysaccharide of the present invention and a treated product thereof.

FIG. 7 shows a schematic diagram illustrating exemplary structures, as expected from the results of the Examples, of the polysaccharide of the present invention and a treated product of the polysaccharide. The structure of the polysaccharide of the present invention is not limited to the structure shown in the schematic diagram of FIG. 7.

There have been many reports stating that pectins extracted from various plants such as herbs have immune stimulating potential. A few reports have been made of the relationship between the immunoreactivity and structure, and it has been reported that a galactan structure contained in the pectins is required for the activity.

In the case of the DEAE-cellulose column adsorbed fraction purified in the Examples, however, a polygalacturonic acid structure was required for the activity. This suggested that the DEAE-cellulose column adsorbed fraction has a mechanism of action different from that of the immune stimulating potential of the pectins having been so far reported.

INDUSTRIAL APPLICABILITY

The present invention makes it possible to obtain a polysaccharide having a high effect on the stimulation of innate immune function and can therefore be widely used in various kinds of foods or drinks, pills, granules, and chewable tablets. The polysaccharide of the present invention is particularly suitable for use as a functional food or specified health food having innate immune stimulating activity in vivo or as an ingredient of a patient diet, nursing diet or the like necessary to address immunological deterioration. Further, the polysaccharide of the present invention can be widely used also as a raw material for medical drugs.

What is claimed is:

1. A polysaccharide having innate immune stimulating activity, comprising:
   25 to 45 parts by mole of galacturonic acid, 20 to 50 parts by mole of galactose, 1 to 7 parts by mole of glucose, 0 to 10 parts by mole of arabinose, 0 to 6 parts by mole of xylose, and 4 to 14 parts by mole of rhamnose as constituent sugars; and
   a polygalacturonic acid chain as a main chain, having α-1,4-linked galacturonic acid.

2. An innate immune stimulant comprising the polysaccharide of claim 1 as an active component.

3. A food or drink comprising the polysaccharide of claim 1.

4. The polysaccharide according to claim 1 comprising:
   25 to 40 parts by mole of galacturonic acid, 30 to 50 parts by mole of galactose, 3 to 7 parts by mole of glucose, 0 to 10 parts by mole of arabinose, 0 to 5 parts by mole of xylose, and 5 to 13 parts by mole of rhamnose as constituent sugars.

5. The polysaccharide according to claim 1 comprising:
   30 to 40 parts by mole of galacturonic acid, 35 to 45 parts by mole of galactose, 5 to 6 parts by mole of glucose, 0 to 5 parts by mole of arabinose, 0 to 5 parts by mole of xylose, and 6 to 12 parts by mole of rhamnose as constituent sugars.

* * * * *